United States Patent
Marrey et al.

(10) Patent No.: US 9,387,100 B2
(45) Date of Patent: Jul. 12, 2016

(54) INTRALUMINAL MEDICAL DEVICE HAVING VARIABLE AXIAL FLEXIBILITY ABOUT THE CIRCUMFERENCE OF THE DEVICE

(75) Inventors: Ramesh V. Marrey, Basking Ridge, NJ (US); Matthew E. Krever, Warren, NJ (US); Daniel Olsen, Califon, NJ (US); Robert Burgermeister, Bridgewater, NJ (US)

(73) Assignee: Cardinal Health Switzerland GmbH (CH)

(*) Notice: Subject to any disclaimer, the term of this patent is extended or adjusted under 35 U.S.C. 154(b) by 361 days.

(21) Appl. No.: 11/620,749

(22) Filed: Jan. 8, 2007

(65) Prior Publication Data

US 2008/0167707 A1 Jul. 10, 2008

(51) Int. Cl.
*A61F 2/06* (2013.01)
*A61F 2/915* (2013.01)
*A61F 2/91* (2013.01)

(52) U.S. Cl.
CPC . *A61F 2/915* (2013.01); *A61F 2/91* (2013.01); *A61F 2002/91558* (2013.01); *A61F 2250/0018* (2013.01); *A61F 2250/0029* (2013.01)

(58) Field of Classification Search
CPC .............. A61F 2002/91558; A61F 2250/0018; A61F 2250/0029; A61F 2/915; A61F 2002/91525; A61F 2002/9158
USPC ................................................ 623/1.15, 1.16
See application file for complete search history.

(56) References Cited

U.S. PATENT DOCUMENTS

| 5,855,600 | A | 1/1999 | Alt | |
|---|---|---|---|---|
| 6,027,526 | A * | 2/2000 | Limon et al. | 623/1.15 |
| 6,287,336 | B1 * | 9/2001 | Globerman et al. | 623/1.3 |
| 6,416,543 | B1 * | 7/2002 | Hilaire et al. | 623/1.16 |
| 6,451,049 | B2 * | 9/2002 | Vallana et al. | 623/1.15 |
| 6,585,757 | B1 | 7/2003 | Callol | |
| 6,610,086 | B1 * | 8/2003 | Kock et al. | 623/1.22 |
| 6,676,697 | B1 * | 1/2004 | Richter | 623/1.16 |
| 6,979,349 | B1 * | 12/2005 | Dang et al. | 623/1.15 |
| 2001/0041930 | A1 | 11/2001 | Globerman et al. | |
| 2004/0002750 | A1 * | 1/2004 | Majercak | 623/1.11 |
| 2005/0149168 | A1 | 7/2005 | Gregorich | |
| 2007/0010872 | A1 * | 1/2007 | Gregorich | 623/1.16 |

FOREIGN PATENT DOCUMENTS

| JP | 2000-24117 | 8/2001 |
|---|---|---|
| JP | 2001-513359 A | 9/2001 |
| WO | WO 98/34668 A | 8/1998 |
| WO | WO 2007/053791 A | 5/2007 |
| WO | WO 2007/082189 A | 7/2007 |
| WO | WO 2008/005111 A | 1/2008 |

OTHER PUBLICATIONS

Office Action in corresponding Japanese Patent Application No. 2012-202435 dated Aug. 5, 2014.
Office Action in corresponding Canadian Patent Application No. 2,618,254 dated Feb. 25, 2014.

* cited by examiner

*Primary Examiner* — Julie A Szpira

(57) ABSTRACT

This invention concerns expandable intraluminal medical devices for use within a body passageway or duct, wherein the devices exhibit differing degrees of flexibility around the circumference of the device.

1 Claim, 10 Drawing Sheets

Single region of high axial stiffness relative to rest of circumference

Single region of low axial stiffness relative to rest of circumference

Regions of high axial stiffness 180 degrees apart

Regions of low axial stiffness 180 degrees apart

Regions of high & low axial stiffness alternating at 90 degree orientations

Low axial stiffness

Axial stiffness increasing from low to high

High axial stiffness

INTRALUMINAL MEDICAL DEVICE HAVING VARIABLE AXIAL FLEXIBILITY ABOUT THE CIRCUMFERENCE OF THE DEVICE

FIELD OF THE INVENTION

This invention concerns an expandable intraluminal medical device for use within a body passageway or duct in which the device has regions that exhibit differing degrees of flexibility about the device.

BACKGROUND OF THE INVENTION

The use of intraluminal prosthetic devices has been demonstrated to present an alternative to conventional vascular surgery. Intraluminal prosthetic devices are commonly used in the repair of aneurysms, as liners for vessels, or to provide mechanical support and prevent the collapse of stenosed or occluded vessels.

Intraluminal endovascular prosthetics involve the percutaneous insertion of a generally tubular prosthetic device, such as a stent, into a vessel or other tubular structure within the vascular system. The stent is typically delivered to a specific location inside the vascular system in a low profile (pre-deployed) state by a catheter. Once delivered to the desired location, the stent is deployed by expanding the stent into the vessel wall. The expanded stent typically has a diameter that is several times larger than the diameter of the stent in its compressed state. The expansion of the stent may be performed by several methods known in the art, such as by a mechanical expansion device (balloon catheter expansion stent) or by self-expansion.

Preferably, a stent would possess a minimum width and wall thickness, which should minimize thrombosis at the stent site after implantation. The preferred stent would also possess sufficient hoop strength to resist elastic recoil of the vessel. Many current tubular stents employ a multiplicity of circumferential sets of strut members connected by either straight longitudinal connectors or undulating longitudinal connecting connectors in an effort to fulfill the above requirements.

The strut members, of which there are ordinarily a plurality that extend around the circumference of the device, can be formed from a number of diagonal sections in turn connected to curved or arced members reminiscent of elbows, thereby forming a zig-zagging structure in a closed ring arrangement. When expanded, the stent provides structural support for the vessel wall. Strut members may be formed from a single piece of metal having a uniform wall thickness and generally uniform strut width. The curved members are formed having a generally uniform wall thickness and generally uniform width.

While the geometry of the stent members is uniform, under load, the strain experienced by each strut member is not. The "stress" applied to the stent across any particular cross section is the force per unit area. These dimensions are those of pressure, and are equivalent to energy per unit area. The stress applied to the stent includes forces experienced by the stent during deployment, and comprises the reactive force per unit area applied against the stent by the vessel wall. The resulting "strain" (deformation) that the stent experiences is defined as the fractional extension perpendicular to the cross section under consideration.

During deployment and in operation, each strut member experiences varying load along its length. High stress and/or strain can cause cracking of the metal and potential fatigue failure of the stent under the stress of a beating heart. It should also be remembered that arteries "pulse" at typically 70 times per minute or more, about 40 million times per year—necessitating that these devices are designed to last in excess of $10^8$ loading cycles for a 10-year life. Thus, guarding against cyclic fatigue failure is a particularly important consideration in stent design. Designs can be physically tested and analytically evaluated to ensure acceptable stress and strain levels are achievable based on physiologic loading considerations. This is typically achieved using the traditional stress/strain-life (S-N) approach, where design and life prediction rely on a combination of numerical stress predictions as well as experimentally-determined relationships between the applied stress or strain and the total life of the component. Fatigue loading for the purpose of this description includes, but is not limited to, axial loading, bending, torsional/twisting loading of the stent, individually and/or in combination. One of skill in the art would understand that other fatigue loading conditions can also be considered.

A bifurcation is a location where the vessel divides into two branches or parts, that is, a main branch vessel and a side branch vessel. One, two, or both branches may exhibit a curvature or bend. The vessel bifurcations generally have circumferential asymmetry. That is, bifurcated vessels generally exhibit asymmetry around their circumference at the point where the main vessel divides into one or more branches. Thus, the opening in the side branch vessel where the side branch vessel joins the main branch vessel may be asymmetrical. The side branch vessel may join the main branch vessel at an oblique angle, which may contribute to the asymmetry of the side branch opening.

In any event, a bifurcation or bend in a vessel can present challenges if an implant is to be deployed there. Where the implant needs to be in a specific orientation (such as for maximizing the therapeutic effect, such as to conform to the bend in one of the main branch or side branch vessels, it would be helpful if the implant were flexible over at least a portion of its surface, so that the device could conform to the bend.

A medical implant, such as a stent, which has circumferential regions that exhibit a relatively high degree of flexibility when compared to other circumferential regions of the device, to exhibit relatively increased flexibility in at least one bending direction while also providing a relative increased degree of stiffness in another bending direction, would be advantageous and advance the state of the art. Such an arrangement, provided for in the implant, would allow the stent to preferentially bend in at least one direction, so the device may conform to curves in the vessels as it traverses in its crimped state on the way to the deployment site, or otherwise in its deployed state conform to the geometry of the vessel at the deployment site, if the implant is deployed at a bend. Likewise, flexibility and conformability are advantageous where the vessel has lesions that render the interior vessel configuration nonlinear.

SUMMARY OF THE INVENTION

The present invention is directed to an expandable intralumenal medical device, such as a medical implant, possessing regions of varying axial flexibility or stiffness along the circumference of the device. In one specific aspect, the present invention is a stent, having substantially cylindrical shape, and the stent is provided with locations of variable axial flexibility, stiffness, or both, at locations about the circumference. That is, the stent can be provided with structure that renders it axially flexible in at least one region of the device circumference, or, in at least one region of the device circumference, axially stiff, or, it can be provided with structural attributes in a plurality of regions that render it both axially flexible and stiff. In yet another specific aspect, the present invention is directed to an expandable intralumenal medical device, for use within a body passageway or duct. The device possesses at least one circumferential region or segment exhibiting greater axial flexibility than at least a second circumferential region of the device. Alternatively, the device possesses at least one circumferential region or segment exhibiting greater axial stiffness than at least a second circumferential region of the device. Again, the expandable intralumenal medical device can be a medical implant such as a stent.

In a particular aspect of the invention, the stent has at least two regions exhibiting a relatively greater degree of axial flexibility than at least two other regions. By way of alternative, the stent has at least two regions exhibiting a relatively greater degree of axial stiffness than at least two other regions. In a more specific aspect of the invention, the regions are positioned in an alternating relationship around the circumference of the device, so that, for example, a given region of relatively greater axial flexibility is positioned between regions of relatively greater axial stiffness (and vice versa).

In a more specific aspect of the invention, the regions exhibiting a relatively greater degree of axial flexibility are positioned to oppose each other across the cross-section of the device, and the regions exhibiting a relatively greater degree of axial flexibility are positioned to oppose each other across the device. In a more specific arrangement, the regions of increased flexibility are positioned 180° from each other, and the regions of increased stiffness are positioned 180° across from each other.

In a specific aspect of the present invention, the medical device can bend in substantially only one direction, owing to the structural attributes and/or construction that provide the device with axially stiff and axially flexible regions. A structural arrangement of this kind can result by arranging the axially stiff and axially flexible regions such that there is only one preferential bending direction of the device. This particular region or side becomes the interior, or short side, of the bend, and is relatively more flexible than other regions of the device.

The device of the present invention, provided with a relatively stiff axial region and a relatively flexible axial region facilitates device orientation, a desirable feature as it travels (1) through curves or bifurcations in the vessel, (2) over curves or bends in the guidewire, or (3) traverses other eccentricities located within the vessel that force the member into a curved path. So long as the device possesses a sufficient degree of freedom to rotate about its longitudinal axis, it will assume the path of least resistance in the course of its travel, and thereby rotate/orient itself to conform to the bend in the vessel. Thus, orientation of the device can be attained as a result of device rotation to align the relatively flexible regions of the device to the bending direction of the vessel or guidewire.

Aside from being adapted to pass relatively easily through bends and curves in the vasculature, the device can be used in a number of beneficial ways. A device, such as a stent that is deployed at the site of or in the vicinity of a bifurcation may have circumferentially asymmetrical design features intended to conform to the bifurcation, and in particular, the side branch ostium. Such devices must be deployed in the proper circumferential orientation, a result that can be obtained by providing the vessel with a relatively stiff region and a relatively flexible region, thereby allowing the device to self-orient to the curve in the vessel. The self-orienting nature is useful where the bend, so to speak, is imparted by the guidewire, which passes through the device. For example, the device may travel over a guide wire passed into a bifurcation side branch, allowing a properly oriented device to be deployed in its in the side branch. In yet another example, a guidewire having a prebent section can be used to effect orientation of the device in situations where vessel characteristics are not of an orientation-producing nature. In other words, by positioning the bend in the guidewire at the desired location, the device will orient itself as it traverses the bend. This arrangement is advantageous where it is desirable to achieve orientation in a relatively straight vessel segment. In any event, with these arrangements, rotation of the device for positioning purposes, whether for deployment or other medically useful purpose is facilitated.

Upon implantation of the medical implant into a vessel of an animal, such as the artery of a human, the implant can be aligned to conform to the vessel shape and geometry. This manifests itself in at least two ways. First, the implant can flex or bend in accordance with curves or bends in the vessel, when in proper alignment with the vessel bend. For instance, the circumferential region of the implant that exhibits a relatively greater degree of axial flexibility can be aligned to curve along with a bend in the artery, thereby conforming to the path of the vessel. In this arrangement, at least one circumferential region of the implant with relatively greater flexibility is in axial tension and one region is in axial compression. Second, due to the presence of lesions, the vessel may exhibit a non-symmetrical cross section at the target site of implantation. Therefore, aligning the stent so that a flexible region is in contact with the lesions would permit the stent to conform to the region where the lesion is present.

The stent of the present invention, possessing circumferential regions of different axial flexibility and stiffness, should be easier to deploy when compared to stents of uniform stiffness/flexibility. The stent can be aligned for delivery through a tortuous arterial pathway in order to provide flexibility in the desired bending plane. The stent would minimize circumferential twisting during the expansion process. Thus, the orientation of the flexible sections or regions of the stent would remain in the same locations after implantation.

It should be understood that a stent is usually delivered in a crimped state via a delivery device, and thus may pass through a curve or bend in a vessel while in the crimped state. The stent of the present invention is capable of flexing to conform to the curve or bend whether in the crimped state, or later, at the time of deployment (and subsequent thereto), when the stent is expanded.

DETAILED DESCRIPTION OF THE INVENTION

Figure 1:
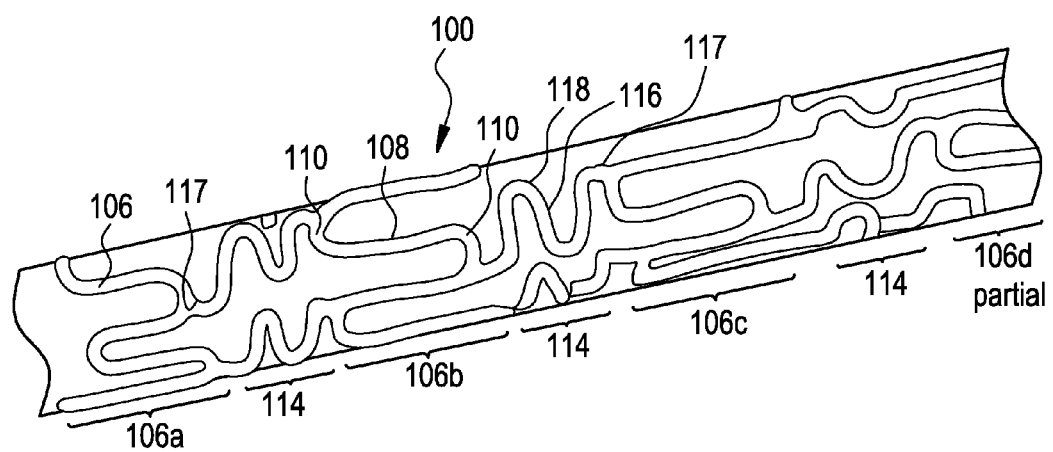
FIG. 1 is a perspective view of an intraluminal stent in an unexpanded or crimped, pre-deployed condition according to one embodiment of the present invention.

FIG. 1 shows an exemplary medical device, here a stent, illustrating a device that can be modified in accordance with the present disclosure. The medical device 100 comprises one or more hoop components 106 having a tubular configuration with proximal and distal open ends defining a longitudinal axis extending therebetween. Each hoop component is formed as a continuous series of substantially longitudinally oriented radial strut members 108 and a plurality of radial arc members 110 connecting adjacent radial struts.

The device of the present invention includes connecting elements 114 joined to longitudinally adjacent hoop components 106. In this specific depiction, adjacent flexible struts 116 are connected at opposite ends in a waveform-like pattern shown here as substantially N-shaped. As illustrated, the plurality of flexible arc members 118 of connecting elements 114 have a substantially semi-circular configuration and are substantially symmetric about their centers, though these specific features should be regarded as essential to the invention.

Figure 2:
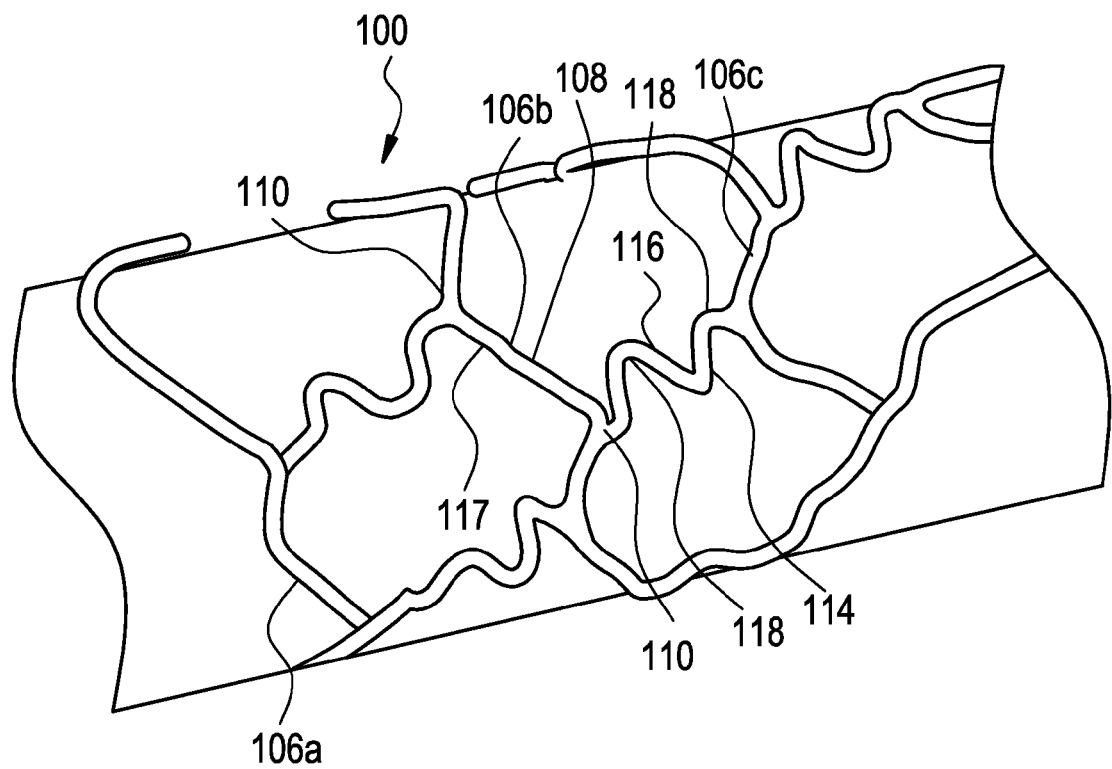
FIG. 2 is a perspective view of an intraluminal stent in the fully expanded condition according to one embodiment of the present invention.

Each connecting element 114 has two ends. One end of connecting elements 114 is attached to the radial arc 110 on one hoop, for example hoop 106(b), and the other end of the connecting element 114 is attached to a second radial arc 110 on an adjacent hoop, for example hoop 106(c). The connecting elements 114 connect longitudinally adjacent hoops 106 (a)-(d) together at to radial arc connection regions 117. FIG. 2 shows the device of FIG. 1 in an expanded state. The device may be expanded by an expansion device, such as a balloon, or it may be made of a self-expandable material, such as nitinol.

Figure 3:
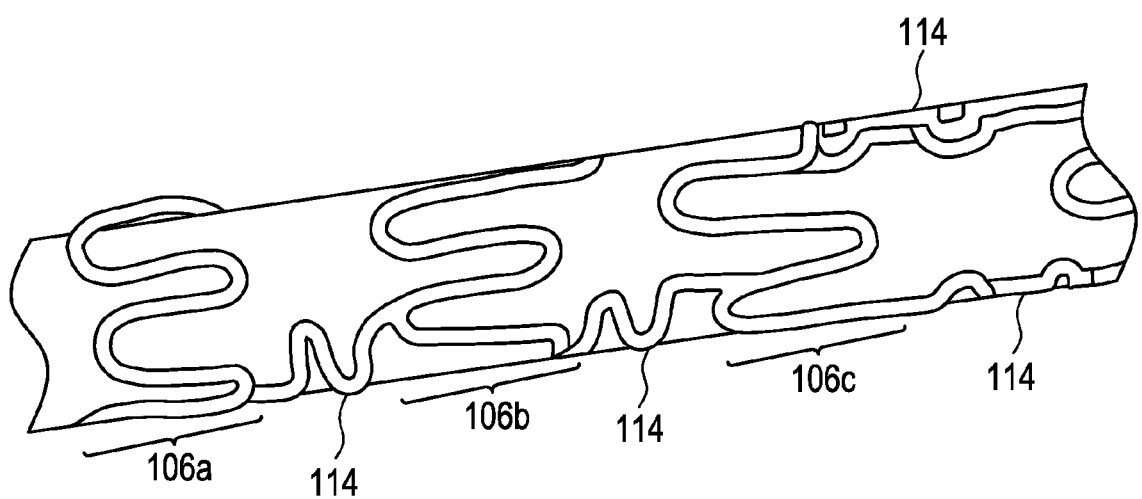
FIG. 3 is a perspective view of an embodiment of the present invention.

The device can be provided with at least one region of axial flexibility greater than at least other region of the device in a number of ways. For instance, by manipulating the number, location, and design parameters of the connecting elements 114, the medical device can be provided with regions of relatively greater axial flexibility and/or with regions of relatively greater axial stiffness. In a first embodiment of the present invention, shown in FIG. 3, a region of relatively greater axial flexibility is formed by omitting the connecting elements 114 to create a flexible segment or region. FIG. 3 shows a device having a relatively flexible circumferential region in which connecting elements 114 have been removed along a line extending lengthwise on the device. The reduction in connecting elements renders the device more flexible in the "removed" region when compared to regions having a relatively greater number of connecting elements 114. FIG. 3 shows that all connecting elements are omitted from the relatively flexible region, though arrangements in which a number of connecting elements are selectively omitted—i.e., less than all connecting elements are omitted—are possible. For example, the connecting elements may be omitted longitudinally from one end of the device to the other, or for a portion of such longitudinal segment. In a further alternative arrangement, the connecting elements may be omitted circumferentially, that is, at locations corresponding to a pattern along the circumference of the device. Likewise, the connecting elements can be omitted from a combination of lengthwise and circumferential locations. In yet another arrangement, the connecting elements is omitted in two locations, across the device from each other, substantially 180° apart.

Figure 4:
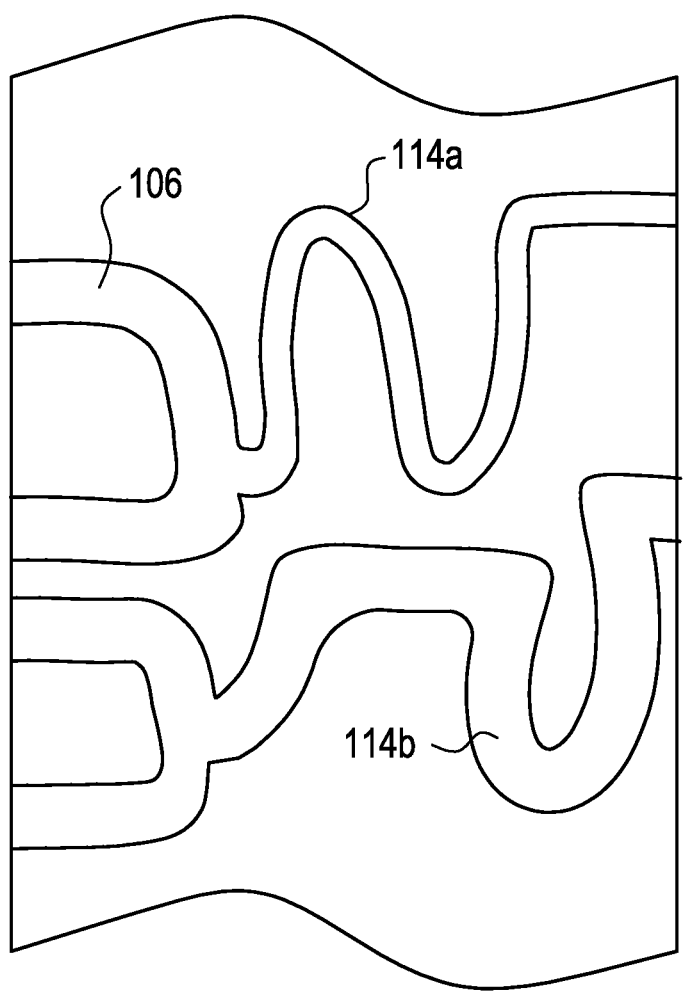
FIG. 4 is a perspective view of another embodiment of the present invention.

FIG. 4 shows an embodiment in which the dimensions of the connecting elements 114, and in particular, the width, depth (or both) of such elements can be reduced in the relatively more flexible regions of the device. FIG. 4 specifically shows a segment along the surface of a device in which connecting elements 114(a) has a relatively smaller width dimension than the width dimension of connecting elements 114(b), and thus connecting elements 114(a) would be expected to exhibit greater flexibility than connecting elements 114(b). The depth of the connecting elements 114(a) can be varied in comparison to the depth of connecting elements 114(b) (or in relation to other connecting elements 114 of the device not shown in the segment) or the amplitude of the connecting element. Furthermore, it should be appreciated that the width, depth, or both of other components, such as the hoop member 106, can also be varied.

Alternatively, the width and/or depth, the amplitude, path length, or combination of any such factors concerning the design of connecting elements 114 can be modified in one circumferential region or segment of the device to provide a region that is relatively axially stiffer than a second circumferential region of the device (or on the other hand, modified to provide for a relatively axially flexible region). For example, connecting elements 114 possessing an increased width and/or depth dimension (when compared to the connecting elements 114 in a second region of the device), will exhibit increased resistance to bending, and thus, exhibits increased stiffness over at least a portion of the surface of the device. Also, the location where the connecting elements join to adjacent hoop members 106 can be selected to modify the flexibility or rigidity of a device segment.

Figure 5:
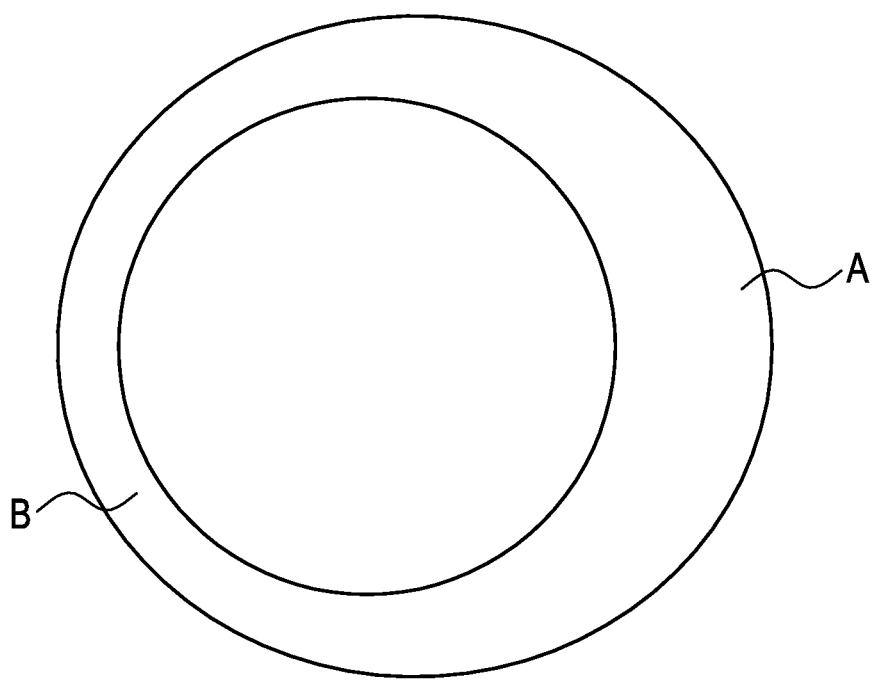
FIG. 5 is a perspective view of yet another embodiment of the present invention.

There are other ways in which the implant can be provided with a circumferential region that is relatively more flexible and/or stiffer than other circumferential regions of the device. For example, the wall thickness of the implant, in a given segment can be larger than in a second region of the implant. FIG. 5 depicts such an arrangement, where region A is radially thicker than region B. It would be expected that the device would be less flexible in thicker region A. Likewise, the wall thickness of the implant in region B renders the device more flexible there than in region A. In this arrangement, the connecting elements 114, hoop components 106, radial strut members 108, and radial arc members 110, flexible struts 116, and flexible arc members 118 in the selected segment can be made either radially thicker or thinner than in a second region of the implant. An implant with varying regions of wall thickness can be produced by extruding a device though a dye exhibiting the desired different wall thickness regions. With this arrangement, a portion of the device, and components comprising same, as described above, will be thicker or thinner, that is, stiffer or more flexible, depending on the dimensions of the dye. Alternatively, a portion of the device can be made thinner by machining or polishing its surface, to create a relatively thinner, and thereby more flexible, region of the device. This works particularly well when the device is produced from a metallic material.

Figure 6:
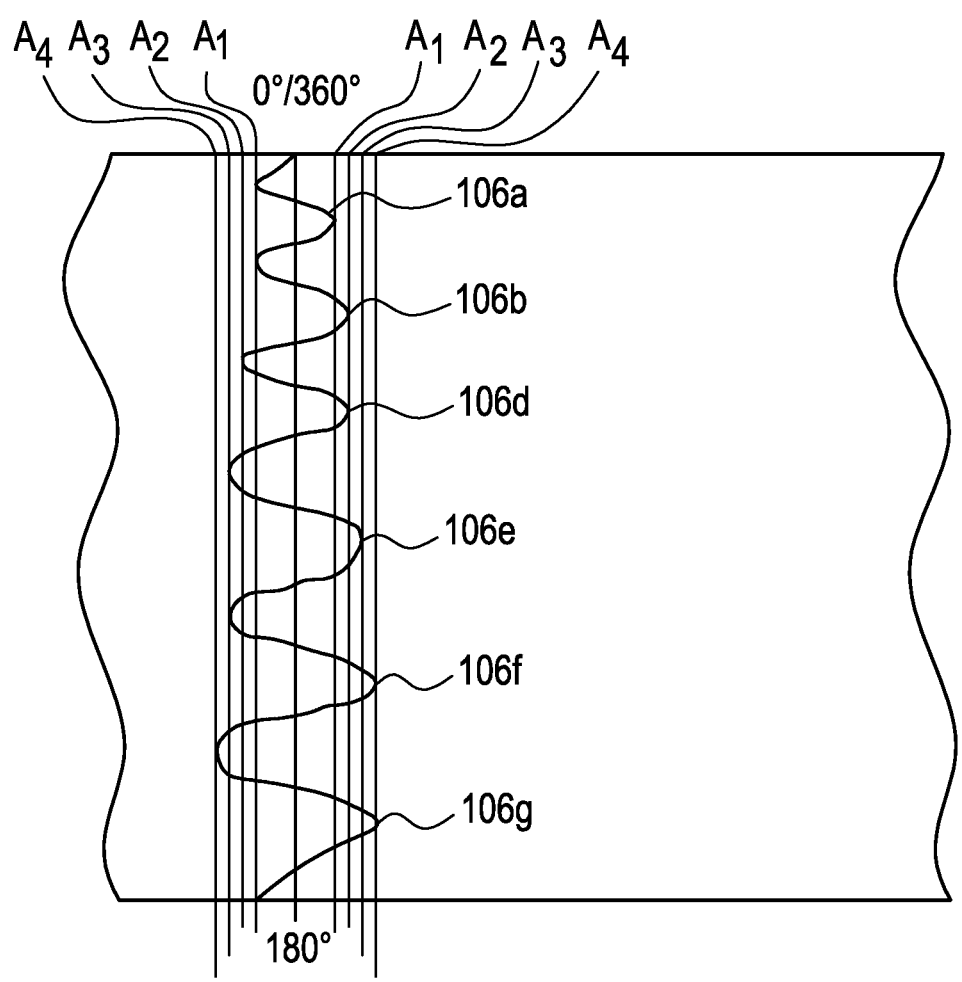
FIG. 6 is a perspective view of yet still another embodiment of the present invention.

In another embodiment, shown in FIG. 6, the amplitude of the hoop components 106 varies over a 180° section of the device. Starting at a location on the device circumference, designated 0°, where the amplitude of the hoop components are at their smallest ($A_1$), and then traversing around the circumference 180°, the amplitude of the hoop component 106(a) increases over the circumference, with the amplitude of hoop components 106(b) to 106(f) gradually increasing, and is largest at hoop component 106(*g*) (A₄). The backside of the device, not shown in FIG. 6, is substantially symmetric with what is shown in the figure. In this arrangement, smaller amplitude hoop components, such as 106(*a*) and 106(*b*), exhibit relatively greater flexibility than larger amplitude hoop components, such as 106(*f*) and 106(*g*).

Figure 7:
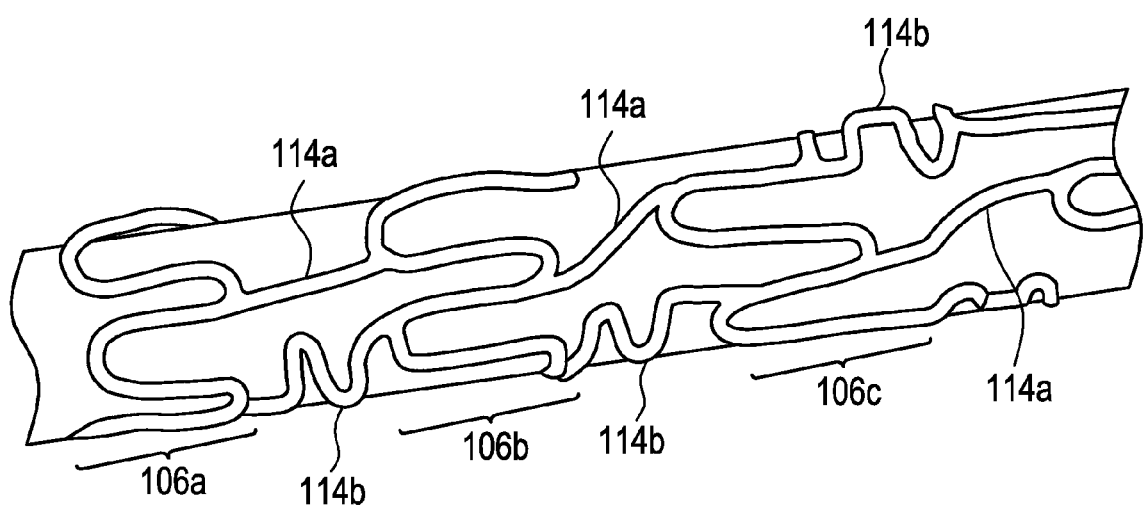
FIG. 7 is a perspective view of yet still another embodiment of the present invention.

In yet another embodiment shown in FIG. 7, the relatively more flexible region of the device is provided with connecting elements 114*b* that are longer than the length of the connecting elements 114*a* found in a second less flexible region of the device. The connecting elements in the second, less flexible region of the device that are relatively straighter, that is, with smaller, whereas in the relatively more flexible sections, the connecting elements exhibit a relatively more tortuous path leading to larger path length, which, thereby can exhibit a greater degree of flexibility. It should be understood that the connecting elements opposite the connecting elements 114*b* may be substantially the same in kind as elements 114*b*, and the connecting elements opposite the connecting elements 114*a* may be substantially the same in kind as elements 114*a*.

Figure 8A:
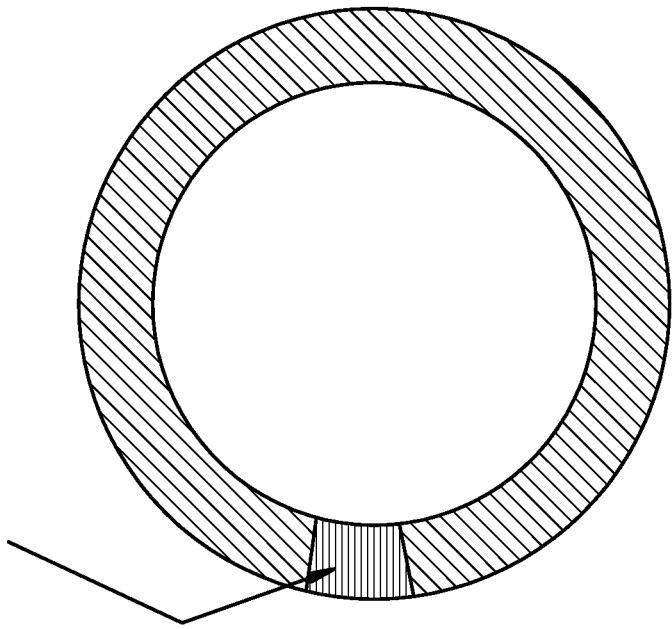
FIGS. 8A-8F depict alternative arrangements for constructing devices of the present invention.
Figure 8B:
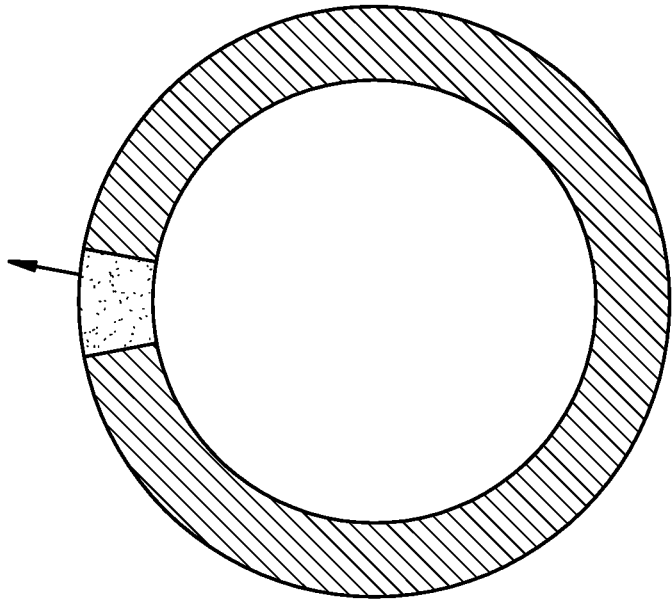

FIGS. 8A-8F illustrate arrangements for positioning regions of relatively greater flexibility and regions of relatively greater stiffness around the circumference of the device. In FIG. 8A, the device is provided with a single region of relatively greater axial stiffness in relation to the remainder of the circumference. In FIG. 8B, the device is provided with a single region of relatively greater axial flexibility in relation to the remainder of the circumference. A stiffening rod that runs longitudinally through a majority of the device's length can provide a degree of stiffness that is greater than exhibited by the remainder of the device's circumference. FIG. 8A shows a device provided with a single region of relatively lesser axial stiffness in relation to the remainder of the device circumference. The region of relatively greater axial stiffness could predominate the device circumference as depicted in FIG. 8B, or it could comprise just a minor portion of the device circumference.

Figure 8C:
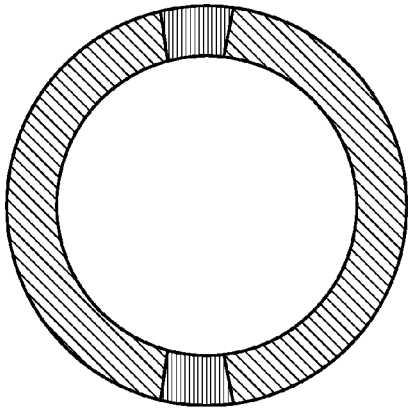
Figure 8D:
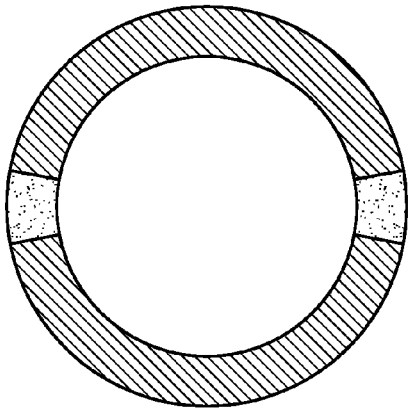
Figure 8E:
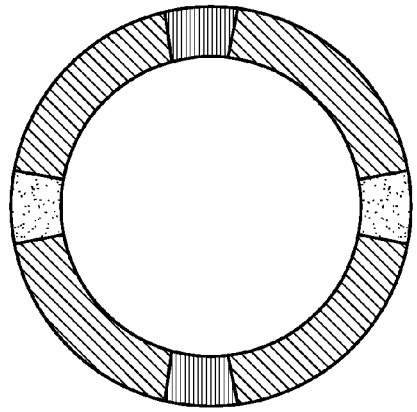
Figure 8F:
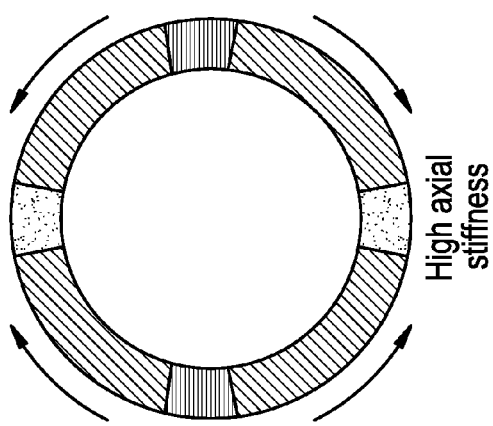

FIG. 8C shows a device in which regions of relatively greater axial stiffness are positioned 180° apart from each other. FIG. 8D shows a device in which regions of relatively greater and relatively higher axial stiffness alternate at 90° orientations. FIG. 8E shows a device in which regions of relatively lower axial stiffness are positioned 180° apart from each other. FIG. 8F shows a device in which axial stiffness increases from high to low across a 90 degree section as device circumference is traversed, or conversely, in which axial flexibility increases from low to high. Any of the aforementioned embodiments can be arranged in the patterns described in the FIG. 8 series.

Figure 9:
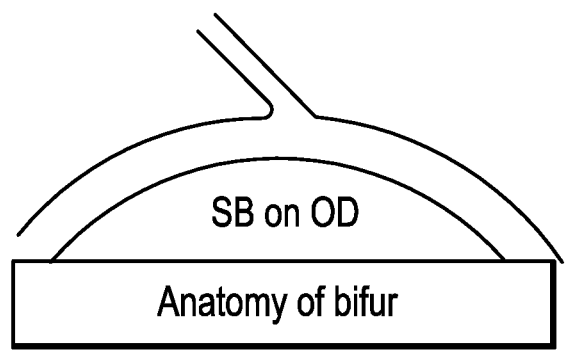
FIG. 9 is a cross sectional view of a first bifurcation configuration in a patient's vasculature.
Figure 10:
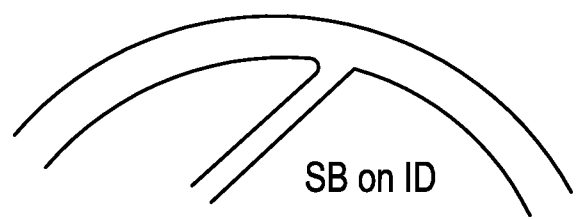
FIG. 10 is a cross sectional view of a second bifurcation configuration in a patient's vasculature.

The device can be used with dissimilar branch arrangements, such as a vessel anatomy having a main branch bend and a side branch off the outside of the main branch bend shown in FIG. 9, and a vessel anatomy having a main branch bend and a side branch off the inside bend on the main branch shown in FIG. 10. By rotating the device it will orient for deployment in the main branch or the side branch ostium, as called for in the course of treatment.

The device may be fabricated by laser machining of a material into a cylindrical device. Suitable materials that can be used to fabricate the stent include, cobalt chromium alloy and other non-ferrous alloys, such as Cobalt and Nickel based alloys, Nickel Titanium alloys, stainless steel, other ferrous metal alloys, refractory metals, refractory metal alloys, titanium and titanium based alloys. The stent may also be fabricated from a ceramic or polymer material.

Therapeutic or pharmaceutical agents may be applied to the device, such as in the form of a drug or drug-eluting layer, or surface treatment after the device has been formed. In a preferred embodiment, the therapeutic and pharmaceutical agents may include any one or more of the following: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $11_b/111_a$ inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

While a number of variations of the invention have been shown and described in detail, other modifications and methods of use contemplated within the scope of this invention will be readily apparent to those of skill in the art based upon this disclosure. It is contemplated that various combinations or sub combinations of the specific embodiments may be made and still fall within the scope of the invention. For example, the embodiments variously shown to be cardiac stents may be modified to treat other vessels or lumens in the body, in particular other regions of the body where vessels or lumen need to be supported. This may include, for example, the coronary, vascular, non-vascular and peripheral vessels and ducts. Accordingly, it should be understood that various applications, modifications and substitutions may be made of equivalents without departing from the spirit of the invention or the scope of the following claims.

What is claimed is:

1. An implantable medical device comprising:

a plurality of hoop components each comprising a plurality of substantially longitudinally oriented radial strut members interconnected via radial arc members, the plurality of hoop components forming a substantially tubular device defined by an axial direction and a circumferential direction, the substantially tubular device having one or more discrete regions of greater or lesser stiffness around the circumference of the device; and a plurality of connecting elements connecting the plurality of hoop components to form a substantially tubular structure, wherein a set of more than one of the plurality of connecting elements have connecting elements that join adjacent corresponding portions of the hoop components and vary in at least one of length, tortuosity, width and depth as compared to adjacent connecting elements in the circumferential direction, thereby cooperating to establish one of the discrete regions of greater or lesser stiffness around the circumference of the device, such that a stiffness at a first discrete region is different than a stiffness at a 90° orientation, wherein the set of more than one of the plurality of connecting elements are in one circumferential region.

* * * * *